United States Patent
Worcel

(10) Patent No.: US 8,328,855 B2
(45) Date of Patent: Dec. 11, 2012

(54) OSTEOSYNTHESIS DEVICE WITH RAPID FIXING MEANS

(76) Inventor: Alexandre Worcel, Montilgnon (FR)

( * ) Notice: Subject to any disclaimer, the term of this patent is extended or adjusted under 35 U.S.C. 154(b) by 98 days.

(21) Appl. No.: 12/846,928

(22) Filed: Jul. 30, 2010

(65) Prior Publication Data

US 2011/0054541 A1     Mar. 3, 2011

Related U.S. Application Data

(63) Continuation of application No. PCT/FR2009/000116, filed on Feb. 2, 2009.

(30) Foreign Application Priority Data

Feb. 1, 2008   (FR) ...................... 08 00556

(51) Int. Cl.
*A61B 17/80*   (2006.01)
(52) U.S. Cl. ...................... 606/290; 606/286
(58) Field of Classification Search .............. 606/54–59, 606/70, 71, 286–291, 294, 264–270
See application file for complete search history.

(56) References Cited

U.S. PATENT DOCUMENTS

| | | | | |
|---|---|---|---|---|
| 6,368,321 B1* | 4/2002 | Jackson | ........................ | 606/270 |
| 6,716,214 B1* | 4/2004 | Jackson | ........................ | 606/266 |
| 2003/0208204 A1* | 11/2003 | Bailey et al. | ..................... | 606/69 |
| 2004/0097935 A1* | 5/2004 | Richelsoph et al. | ............ | 606/61 |
| 2005/0187551 A1 | 8/2005 | Orbay et al. | | |
| 2005/0187552 A1 | 8/2005 | Michelson | | |
| 2005/0228386 A1* | 10/2005 | Ziolo et al. | ...................... | 606/69 |
| 2006/0100621 A1* | 5/2006 | Jackson | ......................... | 606/61 |
| 2010/0042161 A1 | 2/2010 | Worcel | | |
| 2011/0060370 A1 | 3/2011 | Worcel | | |
| 2011/0060371 A1 | 3/2011 | Worcel | | |

FOREIGN PATENT DOCUMENTS

| | | |
|---|---|---|
| EP | 0517939 A1 | 12/1992 |
| WO | 2007138062 A1 | 12/2007 |
| WO | 2008029032 A2 | 8/2009 |
| WO | 2009103886 A2 | 8/2009 |

OTHER PUBLICATIONS

International Search Report for PCT/FR2009/000116, dated Jul. 29, 2009.

* cited by examiner

*Primary Examiner* — Thomas Barrett
*Assistant Examiner* — Si Ming Lee
(74) *Attorney, Agent, or Firm* — Elmore Patent Law Group, PC; Edgar W. Harlan; Carolyn S. Elmore, Esq.

(57) ABSTRACT

The invention relates to an osteosynthesis device having a plate (10) which includes a recess (12) which defines an inner edge (22) and receives ring (14) designed to receive the pin (20). According to the invention, the plate (10) has a threaded opening (26) on the edge of the recess (12), which opens into the inner edge (22), while the ring (14) is slit radially. The device includes a screw (32) that can be screwed through the threaded opening (26) so as to bear against the ring (14) and cause the ring (14) to bear with force against a portion of the inner edge (22) and tighten the ring (14) on the pin (20).

9 Claims, 1 Drawing Sheet

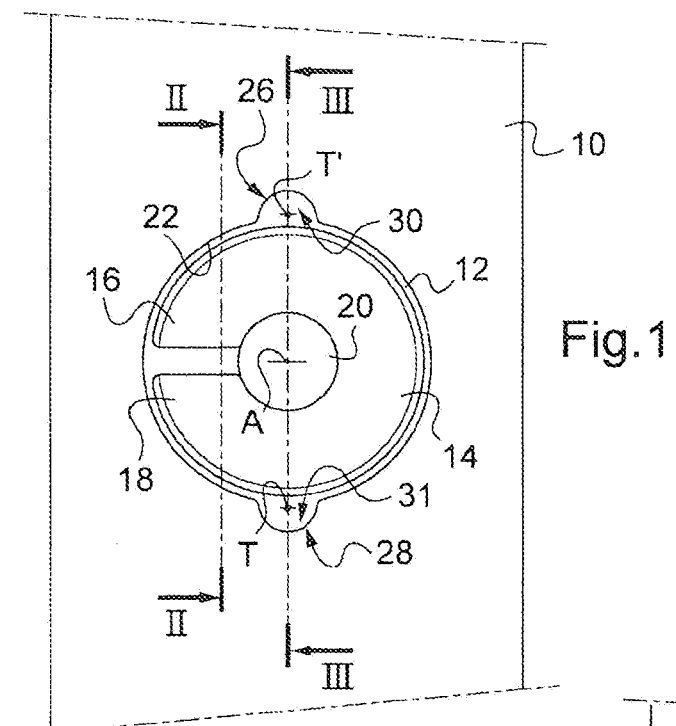
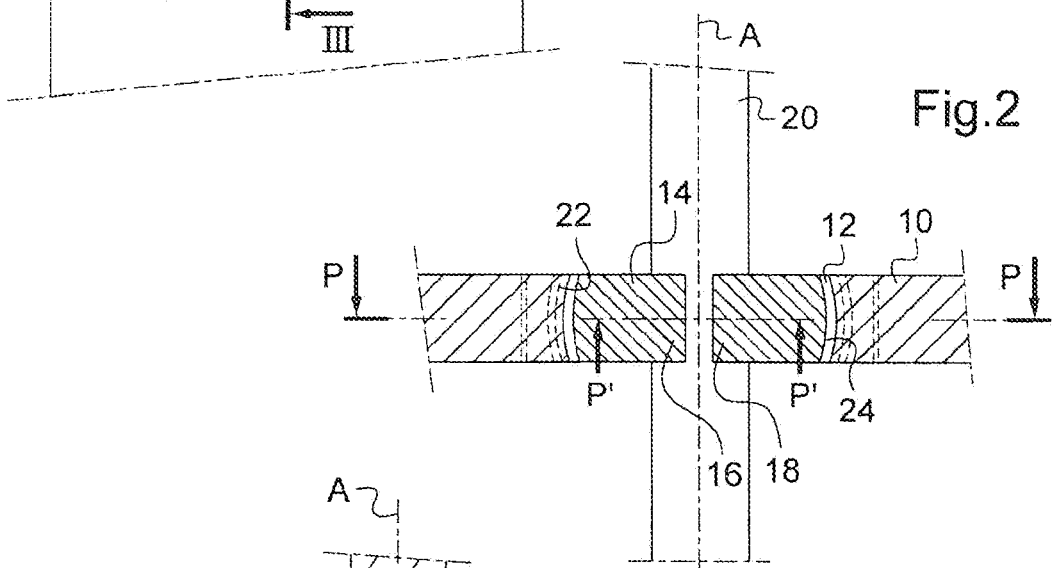
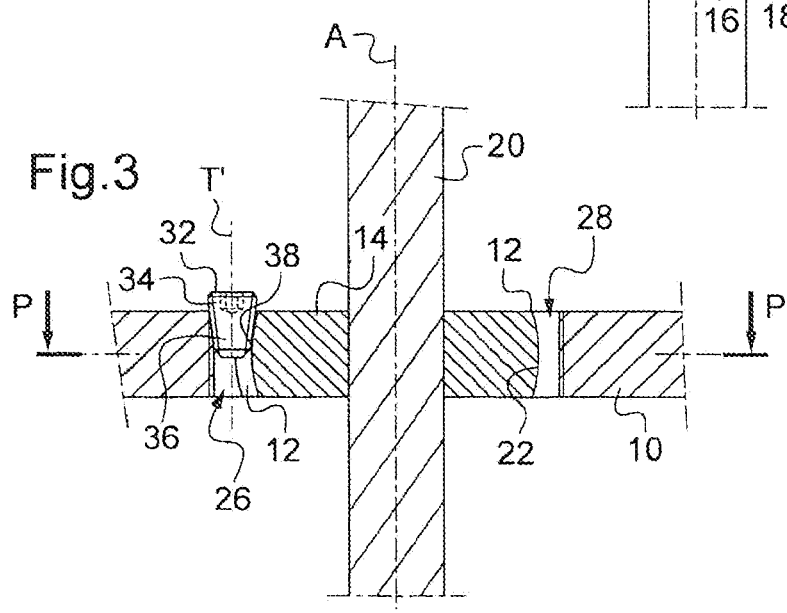

OSTEOSYNTHESIS DEVICE WITH RAPID FIXING MEANS

RELATED APPLICATIONS

This application is a continuation of PCT/FR2009/000116, filed Feb. 2, 2009, which claims the benefit of FR0800556, filed on Feb. 1, 2008. The entire teachings of the above application(s) are incorporated herein by reference.

FIELD OF THE INVENTION

The present invention relates to an osteosynthesis device comprising a plate and fixing means allowing a pin to be held through said plate.

One anticipated field of application is notably that of the reduction of fractures for which the plate extends along two bits of bone delimited by the fracture and at least two pins are installed through the plate and screwed respectively into said two bits of bone. In that way, because the two pins are held in a fixed position the one relative to the other by means of the plate, the two bits of bone are correspondingly held together. A device such as this is generally installed for a set period, of the order of about a month, during which the two bits of bone knit back together.

BACKGROUND OF THE INVENTION

Numerous devices of this type are already known, the plate then having at least two recesses made in its thickness and passing right through it. They are spaced apart in such a way that they can be fitted respectively facing the two bits of bone. The recesses are designed to accept the fixing means of the aforementioned type. They generally comprise a ring or a collar, screw-fitted into the recess. The pin is then mounted through this collar which guides it in a set direction with respect to the plate, for example inclined at an appreciable angle with respect to a perpendicular to the plate. Document EP 1 583 478 for example discloses such a device and the pin is kept in a fixed position with respect to the plate by a locking sleeve in which the pin is engaged, and which is screwed into the collar, around the pin, along an axis that is angularly offset with respect to the axis of the pin. Thus, given this angular offset, the screwing of the locking sleeve gradually causes irreversible locking of the pin with respect to the plate.

That device works well when the pin extends in a direction substantially perpendicular to the plate or in a direction with a relatively small angular offset with respect to said perpendicular direction. By contrast, it is relatively awkward to keep in a fixed position a pin that is inclined through a plate. Furthermore, the pin has to be a precise fit in the locking sleeve which itself has to be fitted into the collar with extremely close tolerances. Hence, machining such parts requires special machine tools and, especially, relatively long manufacturing times with respect to the other mechanical parts of the same type. As a result, they are correspondingly more expensive.

So, one problem that arises and that the present invention aims to address is that of providing an osteosynthesis device which is able not only to hold a pin in a fixed position through a plate in directions that are inclined with respect to the plate, obviously very firmly, but which also is relatively cost-effective to produce.

SUMMARY OF THE INVENTION

With a view to solving this problem, the present invention proposes an osteosynthesis device comprising a plate that can extend along a piece of bone and fixing means for holding a pin through said plate, said pin being screwable into said piece of bone, said plate having a recess made in its thickness to accept said fixing means, said recess defining a closed inner edge, said fixing means comprising a ring intended to accept said pin, said ring being designed to engage with said inner edge and said fixing means further comprising screwable locking means to lock said pin in a fixed position with respect to said plate; according to the invention said plate has at least one threaded opening made at the margins of said recess so as to exhibit an axial aperture opening into said inner edge, while said ring is radially slit so as to be diametrically compressible; and said screwable locking means comprise a screw intended to be screwed through said threaded opening to press against said ring through said axial aperture and cause both said ring to be pressed forcibly against a portion of said inner edge diametrically opposite said threaded opening, and said ring to tighten onto said pin, by virtue of which said pin is held in a fixed position with respect to said plate.

Thus, one feature of the invention lies in the way in which the ring, that can be housed in the recess, collaborates with the pin which is then engaged through the ring, and by virtue of the combined effects of the screwable locking means, which are in the form of screws, and are screwed into a threaded opening that opens partially into the recess and press against the ring as the screw is gradually tightened. In that way, not only is the ring driven against the inner edge of the recess, in a direction substantially parallel to the plate and in a sense diametrically away from the screw but, what is more, thanks to its radial split, the ring can tighten around the pin, wedging it. As a result, the ring is engaged between the screw, which penetrates the recess, and the opposite inner edge thereof, while the pin itself is engaged in the ring. The pin is therefore held in a fixed position with respect to said plate. As will be explained in greater detail in the description that follows, this dispenses with the need for a screw-nut connection between the ring and the plate. Specifically, the ring can then be held in such a position that the mean plane it defines is inclined with respect to the plate. As a result, the pin can be held in a fixed position through the plate at relatively significant inclinations.

Advantageously, the screwable locking means consist of a tapered screw widening from the tip toward the head. Thus, as it is screwed into the threaded opening, the screw pushes laterally with respect to its axis of screwing, through the axial aperture toward the inside of the recess made in the plate, and presses against the ring applying increasing pressure thereto. What is more, because the threaded opening has substantially cylindrical symmetry, the tapered screw applies progressively increasing pressure against the walls of the opening as it is screwed in. When this pressure becomes too great in relation to the screwing effort, the tapered screw locks.

Moreover, said plate has another threaded opening made on the margins of said recess in a position diametrically opposite said at least one threaded opening, so as to allow the pin to be locked in two situations. Specifically, as was explained above, the ring can be held in a position that is inclined with respect to the plate, and this is an advantageous feature of the invention. Hence, taking this inclination into consideration, a greater or lesser portion of ring will extend opposite the axial apertures of the threaded openings. Hence, the threaded opening chosen for the insertion of the screw will be the one for which a greater portion of ring lies facing its axial aperture. In that way, the screw will press better against the ring because it will press over a larger surface area of ring.

Quite obviously, the plate according to the invention is not in any way restricted to two threaded openings, but may have several more of these.

According to one advantageous implementation of the invention, said threaded opening, preferably with cylindrical symmetry, extends substantially perpendicular to said plate, so that the screw can apply significant pressure to the ring without the risk of working loose.

According to one particular embodiment, said threaded opening has an axis of symmetry that is appreciably inclined with respect to a perpendicular to said plate, so that said tapered screw has an extensive portion inside said recess, the generatrix of which is perpendicular to said plate. In that way, the pressure exerted by said extensive portion on the ring is distributed more symmetrically, and the risk of the screw working loose is reduced.

Furthermore, and according to a particularly advantageous embodiment variant, said threaded opening has an axis of symmetry substantially tangential to said inner edge, such that the threaded opening appears like a half cylinder on a circular base with an axial slit. In that way, when a tapered screw is screwed into the threaded opening when it is resting against the ring situated in the recess in the plate, it has a tendency to emerge laterally from its opening through the axial aperture applying pressure to the ring and does not lock by becoming jammed in the opening. By contrast, the pressure applied to the ring is easier to regulate by changing the extent to which the screw is screwed in.

In addition, and with a view to increasing the surface area over which the ring presses against the inner edge in spite of its inclination, said inner edge of said recess is concave so as to form a spherical annulus, whereas said ring defines a spherical segment to act like a ball inside said recess. This increase in bearing surface area not only makes for easier adjustment but also makes the connection between the ring and the plate more firm.

In addition, said ring is advantageously made of a metal that is soft by comparison with said plate, and also by comparison with the screw, so that said screw will self-tap into said ring when forcibly screwed into said threaded opening. Thus, not only does the screw press against the ring, but its threads bite into the material of the ring, holding the ring more firmly in a fixed position with respect to the plate.

For preference, said plate has at least one additional recess spaced away from said recess, said at least one additional recess being intended to accept other fixing means to hold another pin, in exactly the same way as described hereinabove.

BRIEF DESCRIPTION OF THE DRAWINGS

Other particulars and advantages of the invention will emerge from reading the description given hereinafter of one particular embodiment of the invention, given by way of entirely nonlimiting indication and with reference to the attached drawings in which:

FIG. 1 is a partial schematic top elevation of the osteosynthesis device according to the invention;

FIG. 2 is a schematic view of the osteosynthesis device depicted in FIG. 1, in section on II-II;

FIG. 3 is a schematic view of the osteosynthesis device depicted in FIG. 1, in section on III-III.

DETAILED DESCRIPTION OF THE INVENTION

FIG. 1 partially illustrates an osteosynthesis plate 10 in which there is formed a circular recess 12 which passes right through it. A plate such as this quite obviously comprises a plurality of circular recesses staged along its length. Installed in the recess 12 is a circular ring 14 which is radially split so as to form two free ends 16, 18 facing one another. Furthermore, slideably mounted in the ring 14 is a pin 20 of circular cross section. FIG. 2 again shows the osteosynthesis plate 10 in the thickness of which the circular recess 12 is formed. The ring 14 is installed in this circular recess 12 while the pin 20, of longitudinal axis A, is slideably mounted in the ring 14 and oriented in a direction substantially perpendicular to the plane P defined by the plate 10. The ring 14 installed in the plate 10 is also able to guide the pin 20 in a translational movement in a piece of bone when the device is installed on a patient. It will be seen from the figure that the plane P' defined by the ring 14 coincides with the plane P of the plate. Now, when such a device is installed on the patient, these two planes are generally inclined with respect to one another because the ring 14 is significantly pivoted so as to keep the pin 20 inclined with respect to the plate 10.

The circular recess 12 defines a closed inner edge 22 the concave surface of which extends both into the thickness of the plate 10 and over the entire circumference of the recess 12. Furthermore, and correspondingly, the ring 12 has a convex outer edge 24 so that the ring can act as a ball inside the recess 12, as will be explained hereinafter when the device is mounted.

Returning now to FIG. 1 in which the plate 10 has two diametrically opposite threaded openings 26, 28. These openings are made substantially perpendicular to the plate 10 and their threading axis T, T' is tangential to the recess 12 which means that they form two U-shaped housings in the inner edge 22. These threaded openings 26, 28 respectively define an axial aperture 30, 31 which opens into the recess 12.

According to one particular embodiment of the invention, the pin 20 has a diameter of between 0.8 and 5 mm, for example of 4 mm, while the plate 10 has a thickness of between 3 and 7 mm. The circular recess 12 accordingly has a diameter of between 2.5 mm and 15 mm. These elements are, for example, made of stainless steel of the 316L type, which is one of the steels in most widespread use in orthopedic surgery. By contrast, the ring 14 itself is made of a stainless steel that is not as hard.

Reference will now be made to FIG. 3 in order to describe in detail the way in which the osteosynthesis device according to the invention works. This figure shows again, this time in cross section, the osteosynthesis plate 10, the pin 20 engaged in the ring 14 which is itself engaged in the recess 12. By contrast, unlike in FIG. 2, an additional element, a tapered screw 32 of frustoconical shape, made of a surgical steel that is harder than the steel of which the ring 14 is made, has been at least partially screwed into the threaded opening 26. The tapered screw 32 has a widened head 34 in which a hexagon socket has been formed axially to accept a tightening tool, and a tip 36 engaged in the threaded opening 26 and pressing laterally against a first portion 38 of the outer edge 24 of the ring 14.

Thus, a second outer edge portion 24, diametrically opposite the first edge portion 38, presses against an inner edge portion 22 diametrically opposite the tapered screw 32. In this position, the ring 14 is trapped inside the circular recess 12. By contrast, because the tapered screw 32 is not fully engaged in the threaded opening 26, the ring 14 can then pivot inside the circular recess and in directions perpendicular to the plane P of the plate 10 and as a result of this, the inclination of the pin 20 with respect to the plate 10 can be adjusted over a relatively large range of movement. That is an advantage of the invention. When the adjustment has been performed, the tapered screw 32 is then forcibly turned and fully penetrates the thickness of the plate, through the threaded opening 26 and pressing against the ring 14. In that way, as the widened head 34 is gradually screwed in, the ring is driven laterally to press forcibly against the lateral edge portion 22 opposite the tapered screw 32. At the same time, the ring tightens, its two free ends 16, 18 that face one another moving closer together so as to grip and then lock the pin 20 in a fixed position with respect to the ring 14. Hence, because the ring 14 is itself engaged between the inner edge 22 and the tapered screw 32 screwed into the threaded opening 26, the pin 20 is thereby held in a fixed position with respect to the plate 20.

Further, because the ring 14 is made of a material that is softer than the material from which the tapered screw 32 is machined and the plate 10 is cut, the threads of the tapered screw bite into and become embedded in the outer edge 24 of the ring 14 as the screw is gradually screwed in. Because the screw is thus anchored in the ring 14, the latter becomes perfectly firmly secured to the plate 10.

A plate for an osteosynthesis device according to the invention, is intended to be fitted along a fractured piece of bone and to accept a plurality of pins of the aforementioned type in order to hold the various bits of fractured pieces of bone fixedly in position with respect to said plate and therefore hold them in a fixed position relative to one another.

While this invention has been particularly shown and described with references to preferred embodiments thereof, it will be understood by those skilled in the art that various changes in form and details may be made therein without departing from the scope of the invention encompassed by the appended claims.

What is claimed is:

1. An osteosynthesis device comprising a plate (10) that can extend along a piece of bone and fixing means for holding a pin (20) through said plate, said pin (20) being screwable into said piece of bone, said plate (10) having at least two recesses (12) made in its thickness to accept said fixing means, each of said recesses defining a closed inner edge (22), said fixing means comprising a ring (14) intended to accept said pin (20), said ring (14) being designed to engage with said inner edge (22) and said fixing means further comprising screwable locking means (32) to lock said pin (20) in a fixed position with respect to said plate (10);

characterized in that said plate (10) has at least one threaded opening (26) made at the margins of each of said recesses (12) so as to exhibit an axial aperture (30, 31) opening into said inner edge (22), while said ring (14) is radially split so as to be diametrically compressible; and in that said screwable locking means comprise a screw (32) intended to be screwed through said threaded opening (26) to press against said ring (14) through said axial aperture (30, 32) and cause both said ring (14) to be pressed forcibly against a portion of said inner edge (22) diametrically opposite said threaded opening (26), and said ring (14) to tighten onto said pin (20), by virtue of which said pin (20) is held in a fixed position with respect to said plate (10).

2. The osteosynthesis device as claimed in claim 1, characterized in that said screw (32) is a tapered screw of frustoconical shape.

3. The osteosynthesis device as claimed in claim 1, characterized in that said plate (10) has another threaded opening (28) made on the margins of said recess (12) in a position diametrically opposite said at least one threaded opening (26).

4. The osteosynthesis device as claimed in claim 1, characterized in that said threaded opening (26, 28) extends substantially perpendicular to said plate (10).

5. The osteosynthesis device as claimed in claim 1, characterized in that said threaded opening (26, 28) has an axis of symmetry that is appreciably inclined with respect to a perpendicular to said plate (10), so that said screw (32) has an extensive portion inside said recess, the generatrix of which is perpendicular to said plate (10).

6. The osteosynthesis device as claimed in claim 1, characterized in that said threaded opening (26, 28) has an axis of symmetry (T', T) substantially tangential to said inner edge (22).

7. The osteosynthesis device as claimed in claim 1, characterized in that said inner edge (22) of said recess (12) is concave so as to form a spherical annulus, whereas said ring (14) defines a spherical segment to act like a ball inside said recess (12).

8. The osteosynthesis device as claimed in claim 1, characterized in that said ring (14) is made of a metal that is soft by comparison with said plate (10) so that said tapered screw (32) will self-tap into said ring when screwed into said threaded opening (26, 28).

9. The osteosynthesis device as claimed in claim 1, characterized in that said plate (10) has at least one additional recess spaced away from said recess, said at least one additional recess being intended to accept other fixing means to hold another pin.

\* \* \* \* \*